(12) United States Patent
Endo et al.

(10) Patent No.: US 9,060,538 B2
(45) Date of Patent: *Jun. 23, 2015

(54) SOY SAUCE HAVING HYPOTENSIVE EFFECTS AND METHOD FOR PRODUCING THE SAME

(75) Inventors: Yoshikazu Endo, Noda (JP); Shigeki Tanizawa, Noda (JP); Takeharu Nakahara, Noda (JP); Hitomi Aota, Noda (JP); Hiroki Ono, Noda (JP); Yoichi Hanada, Noda (JP); Riichiro Uchida, Noda (JP)

(73) Assignee: KIKKOMAN CORPORATION, Noda-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/519,047

(22) PCT Filed: Dec. 24, 2010

(86) PCT No.: PCT/JP2010/073342
§ 371 (c)(1),
(2), (4) Date: Jun. 25, 2012

(87) PCT Pub. No.: WO2011/078324
PCT Pub. Date: Jun. 30, 2011

(65) Prior Publication Data
US 2012/0282243 A1 Nov. 8, 2012

(30) Foreign Application Priority Data
Dec. 25, 2009 (JP) ................... 2009-295466

(51) Int. Cl.
*A61K 38/05* (2006.01)
*A23L 1/238* (2006.01)
*A23L 1/305* (2006.01)

(52) U.S. Cl.
CPC ............... *A23L 1/238* (2013.01); *A23L 1/3053* (2013.01)

(58) Field of Classification Search
CPC ............................. A23L 1/238; A23L 1/3053
See application file for complete search history.

(56) References Cited

U.S. PATENT DOCUMENTS

| 5,141,756 | A | 8/1992 | Bajracharya et al. |
| 6,054,150 | A * | 4/2000 | Tobe et al. .................. 426/20 |
| 6,974,597 | B2 * | 12/2005 | Ohta et al. ................. 426/590 |
| 2008/0057174 | A1 | 3/2008 | Yamakoshi et al. |
| 2009/0041895 | A1 | 2/2009 | Nielsen et al. |
| 2011/0104334 | A1 * | 5/2011 | Nakahara et al. ............ 426/52 |

FOREIGN PATENT DOCUMENTS

| CN | 101346071 A | 1/2009 |
| CN | 101595972 A | 12/2009 |
| JP | 64-2550 A | 1/1989 |
| JP | 5-260926 A | 10/1993 |
| JP | 2004-8026 A | 1/2004 |
| JP | 2004-290088 | 2/2004 |
| JP | 2004-113098 A | 4/2004 |
| JP | 2006 87328 | 4/2006 |
| JP | 2010 29183 | 2/2010 |
| WO | WO 2004/086880 A1 | 10/2004 |

OTHER PUBLICATIONS

Xu Y. Advances in the Soy Sauce Industry in China, J Ferment Bioeng, 70: 434-439, 1990.*
Nakahara T et al. Antihypertensive Effects of Peptide-Enriched Soy Sauce-Like Seasoning and Identification of Its Angiotension I-Converting Enzyme Inhibitory Substances, J Agric Food Chem, 58: 821-827, 2010.*
Su et al., Effects of temperature and sodium chloride concentration on the activities of proteases and amylases in soy sauce koji, 2005, Journal of Agricultural and Food Chemistry 53(5): 1521-1525.*
Office Action as received in the corresponding Chinese Patent Application No. 201080058992.3 dated Jan. 28, 2013 w/English Translation.
Ding Qi, et al., "Study on Fermentation Technology of Scallop Skirt Sauce", China Academic Journal Electronic Publishing House, 2008, 3:29;3, pp. 1-5.
Office Action issued Jan. 14, 2014, in Japanese Patent Application No. 2011-547647 with English translation.
Haruo Kohama, et al., "Studies on Nitrogenous Compounds in Soy Sauce (part 1) Changes of Amino Acid and Peptides Amounts during Koji in the Process of Soy Sauce Brewing", Tyoumikagaku (Science of seasoning), 12, (2), 1965, pp. 1-6.
Extended European Search Report issued on Dec. 5, 2014 in the corresponding European Application No. 10839554.2.
Emiko Kinoshita, et al., "Purification and Identification of an Angiotensin I-converting Enzyme Inhibitor from Soy Sauce"; Bioscience Biotechnology Biochemistry, vol. 57, No. 7, XP009069711; Jan. 1, 1993; pp. 1107-1110.
Shigehiro Kataoka; "Functional Effects of Japanese Style Fermented Soy Sauce (Shoyu) and Its Components"; Journal of Bioscience and Bioengineering; vol. 100; No. 3; XP027707295; Sep. 1, 2005; pp. 227-234.
Fengxie, J., et al., "Twenty Four Hours Koji-making at soysauce and Miso Industries in China," Journal of Brewing Society in Japan, 91 (7), pp. 478-482, (1996) (with partial English translation).
Xu, Y., "Advances in the Soy Sauce Industry in China," Journal of Fermentation and Bioengineering, 70 (6), pp. 434 to 439, (1990).
International Search Report Issued Feb. 15, 2011 in PCT/JP10/073342 Filed Dec. 24, 2010.

* cited by examiner

*Primary Examiner* — Robert Yamasaki
(74) *Attorney, Agent, or Firm* — Oblon, McClelland, Maier & Neustadt, L.L.P.

(57) ABSTRACT

The present invention provides soy sauce that comprises significant amounts of peptides, and, in particular, hypotensive peptide Gly-Tyr and hypotensive peptide Ser-Tyr, exhibiting a high degree of angiotensin-I-converting enzyme-inhibitory activity and has hypotensive effects while containing no hypotensive agent. Target soy sauce is obtained by mixing soy sauce koji having protease activity of 20 to 300 U/g koji with an aqueous common salt solution and subjecting the mixture to heated digestion, followed by compression filtration. Target soy sauce with a good flavor is obtained by adding soy sauce lactic acid bacteria and soy sauce yeast cells to the moromi mash after heated digestion, and subjecting the resultant to fermentation and maturation, followed by compression filtration.

9 Claims, 3 Drawing Sheets

SOY SAUCE HAVING HYPOTENSIVE EFFECTS AND METHOD FOR PRODUCING THE SAME

This application is a National Stage of PCT/JP10/073342 filed Dec. 24, 2010 and claims the benefit of JP 2009-295466 filed Dec. 25, 2009.

TECHNICAL FIELD

The present invention relates to soy sauce having hypotensive effects that contains no hypotensive agent. More particularly, the present invention relates to soy sauce having hypotensive effects that contains a significant amount of hypotensive peptides and has a high degree of angiotensin-I-converting enzyme-inhibitory activity, which is most characterized by the utilization of soy sauce koji having a low protease activity in combination with heated digestion of such soy sauce koji, and a method for producing the same.

BACKGROUND ART

Methods for producing soy sauce having hypotensive effects, such as a method of adding an inhibitor of the renin-angiotensin system (e.g., nicotianamine), an antiadrenergic agent (e.g., γ-aminobutyric acid), an accelerator of nitric oxide production (e.g., isoflavone), a diuretic substance, a vasodilator substance (e.g., a calcium antagonist), or the like to soy sauce in attempts to attain hypotensive effects from a hypotensive agent (see, for example, Patent Documents 1 and 2), a method of adding a polyphenol (see, for example, Patent Document 3), a method of adding a peptide having angiotensin-I-converting enzyme-inhibitory activity (see, for example, Patent Document 4), and a method of generating and accumulating significant amounts of γ-aminobutyric acids in the soy sauce moromi mash liquid with the use of γ-aminobutyric acid-enriched soybean germs (see, for example, Patent Document 5), have heretofore been known.

However, these techniques are disadvantageous in terms of the necessity of separate production of hypotensive agents, and such hypotensive agents may disadvantageously cause deterioration of soy sauce flavor.

In soy sauce manufacturing, it is necessary for soy sauce manufacturers to work in a dedicated manner to attain high-quality koji, and such high-quality koji is required to have potent enzymatic activity (protease activity, in particular). This is because soy sauce is a seasoning mainly composed of amino acids, and it is necessary to degrade proteins into peptides at first and then thoroughly degrade peptides into amino acids. In the soy sauce industry, therefore, manufacturers search for koji mold that secretes potent protease, adequately treat raw materials for koji to thoroughly develop and propagate koji mold, and intend to maximize enzymatic activity.

In conventional soy sauce manufacturing techniques, accordingly, minimization of protease secretion by koji mold during koji-making and utilization of soy sauce koji having a low protease activity for the production of soy sauce having hypotensive effects are unknown.

Meanwhile, a method of subjecting soy sauce koji to heated digestion at 45° C. to 60° C. for 3 to 8 hours to shorten the soy sauce production time (i.e., fast-brewing) is known (see, for example, Patent Document 6).

Specifically, in the above method, soy sauce koji with the accelerated protease-producing ability is used, and such koji is subjected to heated digestion to rapidly degrade moromi mash components, and, in particular, proteins, thereby rapidly brewing soy sauce in which 50% of total nitrogen is accounted for by α-amino nitrogen and which is rich in aroma.

However, an increase of peptide (non-α-amino nitrogen) content in soy sauce cannot be expected from the above method.

In soy sauce manufacturing techniques, accordingly, increasing peptide content to obtain soy sauce having hypotensive effects is unknown.

Meanwhile, peptides are known to generally have endogenous opioid effects, immunoregulatory effects, effects of accelerating calcium absorption, effects of inhibiting elevated cholesterol, angiotensin-I-converting enzyme (ACE)-inhibitory activity, antioxidative effects, anti-cancer effects, and other effects (see, for example, Patent Document 7 and Non-Patent Document 1).

Also, given dipeptides (i.e., Gly-Tyr and Ser-Tyr) are known to have angiotensin-I-converting enzyme-inhibitory activity and hypotensive effects (hereafter, may be occasionally referred to as "hypotensive peptide Gly-Tyr" or "hypotensive peptide Ser-Tyr") (see, for example, Non-Patent Document 2).

When patients with high normal blood pressure and patients with mild hypertension ingest low-salt soy sauce containing 48 μg/ml and 32 μg/ml hypotensive peptides Gly-Tyr and Ser-Tyr, respectively, for 8 continuous weeks, the systolic blood pressure and the diastolic blood pressure of such subjects are significantly lowered compared with the case when they ingest general low-salt soy sauce (see, for example, Non-Patent Document 3).

If significant amounts of peptides, and, in particular, hypotensive peptides Gly-Tyr and Ser-Tyr, are integrated into soy sauce during production and soy sauce containing large quantities thereof can be obtained, accordingly, soy sauce containing no hypotensive agent and having hypotensive effects can be produced. While such techniques are considered to be a great contribution to the soy sauce industry, they are unknown.

When soy sauce koji is mixed with an aqueous common salt solution, in general, the enzymes of koji satisfactorily function, satisfactorily degrade proteins and starch, and produce very slimy, thick moromi mash. Since peptides generated and accumulated in the liquid of such moromi mash are further degraded into amino acids during the process of fermentation and maturation of the moromi mash, such peptides gradually disappear as moromi mash maturation advances.

Accordingly, it is difficult to retain such peptides, and, in particular, hypotensive peptides Gly-Tyr and Ser-Tyr, until the final form of a soy sauce product is obtained.

Also, soy sauce cake obtained by squeezing the soy sauce moromi mash is known to contain substances exhibiting angiotensin-I-converting enzyme-inhibitory activity (hereafter, may be referred to as "ACE inhibitory activity") (see, for example, Patent Document 7).

Substances exhibiting ACE inhibitory activity are peculiar to soy sauce cake, and such substances are not found in soy sauce. Accordingly, hypotensive effects attained by the ACE inhibitory activity of peptides contained in general soy sauce are very faint, and it is difficult to impart hypotensive effects to soy sauce not containing a hypotensive agent.

PRIOR ART DOCUMENTS

Patent Documents

Patent Document 1: JP Patent Publication (Kokai) No. 2004-290129 A

Patent Document 2: JP Patent Publication (Kokai) No. 2006-136262 A
Patent Document 3: JP Patent Publication (Kokai) No. 2004-194515 A
Patent Document 4: JP Patent Publication (Kokai) No. 2004-290088 A
Patent Document 5: JP Patent Publication (Kokai) No. H11-151072 A (1999)
Patent Document 6: JP Patent No. 2,659,105
Patent Document 7: JP Patent Publication (Kokai) No. H05-279263 A (1993)

Non-Patent Documents

Non-Patent Document 1: Wenyi, Wang et al., Comprehensive Reviews in Food Science and Food Safety, 2005 (4), pp. 63-78
Non-Patent Document 2: K. Suetsuna, J. Nutr. Biochem., 1998 (9), pp. 415-419
Non-Patent Document 3: Jpn. Pharmacol. Ther. (*Yakuri to chiryo*), vol. 36, No. 9, 2008, pp. 837-849

SUMMARY OF THE INVENTION

Problem to be Solved by the Invention

An object of the present invention is to obtain soy sauce containing no hypotensive agent and having high degrees of angiotensin-I-converting enzyme-inhibitory activity and hypotensive effects, which can generate and accumulate significant amounts of peptides, and, in particular, hypotensive peptides Gly-Tyr and Ser-Tyr, in soy sauce moromi mash.

Means for Solving Problem

The present inventors have conducted concentrated studies in order to attain the above object. They used soy sauce koji having protease activity of 20 to 300 U/g koji, mixed the same with an aqueous common salt solution, and subjected the mixture to heated digestion. As a result, they discovered that soy sauce containing significant amounts of hypotensive peptides Gly-Tyr and Ser-Tyr, which have been known to have hypotensive effects, and having a high degree of ACE inhibitory activity could be obtained. Furthermore, they discovered that such soy sauce koji could be obtained by inoculating a seed koji mold onto raw materials for soy sauce koji-making, controlling the period of time for koji-making significantly shorter than that used for the usual procedure (i.e., 20 to 36 hours), and finishing the koji-making (completion of koji-making is referred to as "de-koji") while the koji remains significantly immature ("semi-aged koji"). The present invention has been completed based on such findings.

Specifically, the present invention concerns soy sauce having hypotensive effects and the method for producing the same described below.

(1) Soy sauce having hypotensive effects obtained by a method comprising a step of mixing soy sauce koji having protease activity of 20 to 300 U/g koji with an aqueous common salt solution to prepare soy sauce moromi mash and a step of subjecting the soy sauce moromi mash to heated digestion.

(2) The soy sauce according to (1), wherein the angiotensin-I-converting enzyme (ACE)-inhibitory activity ($IC_{50}$) is 3.0 μl/ml or less.

(3) The soy sauce according to (1) or (2), wherein the soy sauce having hypotensive effects comprises 78 μg/ml or more hypotensive peptide Gly-Tyr and 20 μg/ml or more hypotensive peptide Ser-Tyr.

(4) A food or beverage product having hypotensive effects, which comprises the soy sauce according to any of (1) to (3).

(5) A method for manufacturing soy sauce having hypotensive effects comprising a step of mixing soy sauce koji having protease activity of 20 to 300 U/g koji with an aqueous common salt solution to prepare soy sauce moromi mash and a step of subjecting the soy sauce moromi mash to heated digestion.

(6) A method for manufacturing soy sauce having hypotensive effects comprising a step of mixing soy sauce koji having protease activity of 20 to 300 U/g koji, a protein raw material not subjected to koji-making, and an aqueous common salt solution to prepare a soy sauce moromi mash and a step of subjecting the soy sauce moromi mash to heated digestion.

(7) The method for manufacturing soy sauce according to (5) or (6), wherein the step of heated digestion comprises subjecting the soy sauce moromi mash to heated digestion at 45° C. to 55° C. for 1 to 5 days.

(8) The method for manufacturing soy sauce according to any of (5) to (7), which further comprises a step of adding soy sauce lactic acid bacteria and/or yeast cells to the soy sauce moromi mash subjected to heated digestion in the step of heated digestion and subjecting the resultant to fermentation and maturation.

Effects of the Invention

According to the present invention, soy sauce containing no hypotensive agent, capable of generating and accumulating significant amounts of peptides, and, in particular hypotensive peptides Gly-Tyr and Ser-Tyr, in soy sauce moromi mash, having a high degree of angiotensin-I-converting enzyme-inhibitory activity, and having hypotensive effects can be easily obtained.

EMBODIMENTS FOR CARRYING OUT THE INVENTION

In the present invention, any soy sauce koji can be used, provided that such soy sauce koji is obtained by adding a starch raw material to a protein raw material, inoculating a seed koji mold thereon, and incubating the resultant to produce koji (koji-making), and has protease activity of 20 to 300 U/g koji (in general, soy sauce koji contains 25% to 35% w/w water after the completion of koji-making). The term "U/g koji" used herein refers to protease activity (U) per g of soy sauce koji (wet weight).

For example, soy sauce koji is obtained by adding a starch raw material to a protein raw material, inoculating a seed koji mold thereon, controlling the koji-making at 20° C. to 35° C., and preferably 25° C. to 30° C., for 20 to 36 hours, and finishing (completion of koji-making is referred to as "de-koji") the koji-making (completion of koji-making is referred to as "de-koji") while the koji remains immature ("semi-aged koji"). If the period of time for koji-making is shorter than 20 hours, the resulting koji has substantially no protease activity. This disadvantageously reduces the raw material utility ratio, in particular, nitrogen utility ratio (the ratio of the amount of the total nitrogen dissolved in the moromi mash liquid to the amount of the total nitrogen of raw material) and it is thus unpreferable. If the period of time is longer than 36 hours, however, protease activity is enhanced, the object of the present invention cannot be attained, and it is thus unpreferable.

Examples of protein raw materials include soybean, defatted soybean meal, and wheat gluten. Examples of starch raw materials include wheat plants, such as wheat, barley, rye, and adlay. A mixture of a protein raw material with a starch raw material is used as a starting material for soy sauce koji. The mixing ratio is preferably 30:70 to 70:30, and more preferably 40:60 to 60:40. Moisture content is preferably 35% to 50% (w/w), and more preferably 40% to 45% (w/w).

Examples of seed koji mold include those used for soy sauce manufacturing, such as *Aspergillus sojae* and *Aspergillus oryzae*.

It is very important in the present invention to use soy sauce koji having protease activity of 20 to 300 U/g koji, and preferably 20 to 235 U/g koji. When soy sauce koji having protease activity of 20 U/g or less is used, specifically, the nitrogen utility ratio (i.e., the raw material utility ratio) in soy sauce production is low, and the amount of soy sauce obtained from the starting material is disadvantageously decreased. In contrast, soy sauce koji having protease activity of greater than 300 U/g koji is not preferable since the amount of hypotensive peptides Gly-Tyr and Ser-Tyr generated and accumulated and the degree of angiotensin-I-converting enzyme inhibitory activity are drastically lowered.

In order to implement the present invention, an aqueous common salt solution is then mixed with the soy sauce koji (hereafter, it may be referred to as "shikomi") to prepare soy sauce moromi mash. At the time or initial stage of shikomi (from the following day to up to 10 days after shikomi), protein raw materials that has not yet been subjected to koji-making (plant-derived protein raw materials, such as soybean or wheat gluten) may be added to soy sauce moromi mash. It is preferable that the amount of such raw materials added be 20% (w/w) or less that of the soy sauce koji, so as to achieve a flavor as similar as possible to that of soy sauce prepared via traditional manufacturing techniques.

The amount of aqueous common salt solution is determined so as to bring the common salt concentration in the moromi mash liquid to 5% to 20% (w/v), and preferably 8% to 16% (w/v), and it is added in an amount of 100% to 300% (v/w) relative to the weight of soy sauce koji (wet weight).

Subsequently, the mixture is introduced into a container in which temperature can be controlled and heated digestion is then performed.

In the present invention, heated digestion is also important. When heated digestion is not carried out, peptides generated and accumulated in the moromi mash liquid, and, in particular, hypotensive peptides Gly-Tyr and Ser-Tyr, are further degraded into amino acids and gradually disappear during the process of fermentation and maturation of moromi mash.

It is preferable that heated digestion is carried out at 45° C. to 55° C. for 1 to 5 days.

If temperature is lower than 45° C. or the reaction time is shorter than the aforementioned time, peptides generated in the moromi mash gradually disappear as moromi mash maturation advances, and peptide content is lowered in the end. Thus, such conditions are not preferable. If temperature is higher than 55° C. or the time is longer than 5 days, the color of the digested liquid (soy sauce) is deepened, an odor resulting from warm brewing remains thereon, and flavor deteriorates. Thus, such conditions are not preferable.

In the present invention, it is very important to involve the use of soy sauce koji having a protease activity of 20 to 300 U/g koji in combination with the heated digestion of soy sauce moromi mash. When either one thereof is employed, it is not preferable since the object of the present invention cannot be attained.

Moromi mash subjected to heated digestion can be sufficiently used as a soy-sauce-like seasoning without any processing (such "soy-sauce-like seasoning" is one embodiment of the "soy sauce" of the present invention). Moromi mash subjected to heated digestion may be adequately subjected to compression filtration, pasteurization, racking (clarification), or other procedures in accordance with conventional techniques, and the resultant can be used as the soy sauce of the present invention.

The moromi mash subjected to heated digestion is regulated in terms of salt concentration, so that the common salt content in the moromi mash liquid becomes 12% to 20% (w/v) after fermentation and maturation. Thereafter, lactic acid fermentation is carried out by inoculating soy sauce lactic acid bacteria on the moromi mash to sufficiently propagate lactic acid bacteria, or alcohol fermentation is carried out by inoculating soy sauce yeast cells on the moromi mash to sufficiently propagate yeast cells, or lactic acid fermentation and alcohol fermentation described above are carried out in such order, followed by maturation. Such procedure is preferable because it can yield an improved flavor, compared with the flavor immediately after heated digestion.

Lactic acid fermentation is carried out by adding lactic acid bacteria and maintaining the temperature of the moromi mash at 20° C. to 30° C. for a period of time sufficient to bring the pH level to 4.7 to 5.3 (e.g., approximately 7 to 60 days) to sufficiently propagate lactic acid bacteria for fermentation.

Yeast fermentation is carried out by adding yeast cells and maintaining the temperature of the moromi mash at 20° C. to 35° C. for a period of time sufficient to bring the alcohol content to about 0.5% to 4% (v/v) (e.g., approximately 7 to 90 days) for fermentation and maturation.

Thereafter, compression filtration, pasteurization, racking (clarification), or other procedures are carried out in accordance with conventional techniques. Thus, the soy sauce of the present invention, which has been subjected to fermentation and maturation after heated digestion, is obtained.

The soy sauce obtained by the present invention has ACE inhibitory activity ($IC_{50}$) of 3.0 µl/ml or less. Such soy sauce contains 78 µg/ml or more hypotensive peptide Gly-Tyr and 20 µg/ml or more hypotensive peptide Ser-Tyr, and hypotensive effects can thus be expected. The upper limit of the concentration of Gly-Tyr and Ser-Try is 300 µg/ml in the soy sauce obtained by the present invention.

Accordingly, the soy sauce of the present invention may be added to liquid seasonings, such as various types of soup (e.g., noodle soup ("mentsuyu")), basting sauces (e.g., sauce for broiled meat), ponzu sauces, sauces, dressings, or soups, and fishery or livestock meat products (e.g., fish sausages or hams) in that state (i.e., in a liquid state) or in the form of a paste, solid, or powder obtained by lyophilization, spray drying, or drum drying in accordance with conventional techniques. Thus, food and beverage products for which hypotensive effects can be expected can be obtained.

Several techniques for measurement of ACE inhibitory activity are known as described below, and such activity can be measured by any such techniques:

the method of Kasahara et al. (Y., Kasahara, Clinical Chemistry, 11, 1981, 27, pp. 1922-1925);

the method of Cushman et al. (D. W., Cushman et al., Biochemical, Pharmacology, 1971, (20), pp. 1637-1648);

the method of Yamamoto (Journal of the Japan Society of Chest Diseases, 1980, (20), pp. 297-302, Examination of methods for assaying serum angiotensin-converting enzyme activity); and the method of Lieberman (Lieberman, Am. J. Med., 1975, (59), pp. 365-372).

Specifically, ACE inhibitory activity ($IC_{50}$) can be assayed via the following procedures.

The soy sauce of the present invention is allowed to pass through a solid-phase extract apparatus filled with a reversed-phase solid-phase extracting agent and washed with a 0.1% (v/v) trifluoroacetic acid (TFA) aqueous solution to remove nicotianamine fractions.

Subsequently, a 60% (v/v) acetonitrile aqueous solution (containing 0.1% (v/v) TFA) is allowed to pass through the solid-phase extract apparatus to elute peptides.

The eluate is solidified to dryness via centrifugation and redissolved with ultrapure water to obtain samples (peptide fractions).

The concentration of the sample exhibiting a 50% ACE inhibitory rate in an ACE-based enzyme reaction system is converted into the concentration of soy sauce before treatment by the solid-phase extraction apparatus, and the determined value is used to designate the ACE inhibitory activity ($IC_{50}$) of soy sauce.

Hereafter, the present invention is described in detail with reference to the examples, although the present invention is not limited to the examples.

EXAMPLE 1

Method for Soy Sauce Manufacturing Comprising Performing Heated Digestion with the use of Low-Protease Soy Sauce Koji, Followed by Fermentation and Maturation Warm water (80° C.) was sprinkled on defatted soybeans (14 kg) (130% (w/w)), and the resultant was heated and steam-boiled under pressure using saturated water vapor at a steam pressure of 2 kg/cm$^2$ (gauge pressure) for 20 minutes to obtain steamed, defatted soybean.

Separately, raw wheat (6 kg) was roasted and milled in accordance with a conventional technique.

Subsequently, the two processed raw materials were mixed to prepare a koji-making raw materials with a moisture content of approximately 40% (w/w). A bran seed koji of *Aspergillus oryzae* (ATCC14895) (effective spore count: 1×10$^9$ spores/g) was inoculated thereon in an amount of 0.1% (w/w), koji-making was controlled in accordance with a conventional technique at 20° C. to 35° C., and koji-making was terminated within the time shown in Table 1 to obtain soy sauce koji having various protease activity.

An aqueous common salt solution (about 1.2 liters) was mixed with 0.8 kg of the resulting soy sauce koji, so as to bring the common salt concentration in the moromi mash liquid to 13.0% (w/v) after digestion, and the resultant was subjected to digestion at 50° C. for 72 hours while being adequately stirred. Thus, the digested moromi mash was obtained.

Subsequently, the digested moromi mash was cooled to room temperature (about 20° C.), soy sauce lactic acid bacteria (*Tetragenococcus halophilus*) were added at 1×10$^5$ cells/g of moromi mash, and lactic acid fermentation was carried out at 20° C. for 3 weeks to obtain soy sauce moromi mash having a pH of about 5.2.

Subsequently, soy sauce yeast cells (*Zygosaccharomyces rouxii*) were added at 5×10$^5$ cells/g of moromi mash, and fermentation and maturation were conducted at 25° C. for 1 month while conducting aeration in accordance with a conventional technique, according to need.

Subsequently, the matured moromi mash was subjected to compression filtration, the resulting raw soy sauce was subjected to pasteurization at 80° C. for 30 minutes, and the resultant was introduced into a clarification tank and subjected to racking for 3 days therein, so as to obtain various soy sauce products with good clarity and flavor.

The obtained soy sauce products were subjected to measurement of the nitrogen utility ratio, components (TN (total nitrogen) and NaCl), hypotensive peptides, and ACE inhibitory activity ($IC_{50}$) in accordance with the methods described below. The results are shown in Table 1 and FIG. 1.

Soy sauce is known to contain nicotianamine as an ACE inhibitor, in addition to peptides. Accordingly, in order to accurately measure the ACE inhibitory activity originating from soy sauce peptides, a nicotianamine fraction was firstly removed from the soy sauce by pretreatment with the use of a solid-phase extraction apparatus filled with a reversed-phase solid-phase extraction agent (e.g., octadecyl-silylated silica gel), such as a reversed-phase solid-phase extraction cartridge column (e.g., Sep-Pak Plus C18, Waters), thereafter, the soy sauce after the pretreatment was subjected to analysis of ACE inhibitory activity ($IC_{50}$). Thus, the ACE inhibitory activity originating from the soy sauce peptides could be accurately analyzed.

(1) Method for Measuring Nitrogen Utility Ratio in Soy Sauce Production

Measurement was carried out with reference to the method for measuring nitrogen utility ratio in soy sauce moromi mash of the "Experimental Method for Soy Sauce" (THE JAPAN SOY SAUCE INSPECTION INSTITUTE, date of issue: Mar. 1, 1985).

(2) Method for Measuring Protease Activity

Measurement was carried out with reference to the method for measuring enzyme activity (total protease) of the "Experimental Method for Soy Sauce" (THE JAPAN SOY SAUCE INSPECTION INSTITUTE, date of issue: Mar. 1, 1985).

Specifically, the reaction was carried out using milk casein as a substrate at pH 7.0, the generated non-proteinous substances were assayed via the Folin colorimetric method, the amount of enzymes that liberate non-proteinous substances equivalent to 1 µg of tyrosine per minute was designated as "1 unit," and the activity was determined per g of soy sauce koji.

(3) Component Analysis of Soy Sauce

Total soluble nitrogen (TN) was assayed with the use of the 1035 Kjeltec autosampler system (Actac Co., Ltd.) in accordance with a conventional technique.

NaCl was assayed in accordance with the method for measuring common salt content of the soy sauce testing method (THE JAPAN SOY SAUCE INSPECTION INSTITUTE; date of issue: Mar. 1, 1985).

(4) Method for Measuring Hypotensive Peptides Gly-Tyr and Ser-Tyr

Measurement was carried out with the addition calibration technique using the LC-MS/MS system 2695, QuattroMicro API (Waters).

(5) Method for Measuring ACE Activity ($IC_{50}$)

Samples (100 µl) were applied to Sep-Pak® Plus C18 Environmental Cartridges (Waters) and then washed with 4 ml of a 0.1% (v/v) trifluoroacetic acid (TFA) aqueous solution to remove nicotianamine fractions.

Subsequently, 5 ml of a 60% (v/v) acetonitrile aqueous solution (containing 0.1% (v/v) TFA) was allowed to pass through the column to elute peptides, the eluate was solidified to dryness via centrifugation, and the resultant was redissolved in 1 ml of ultrapure water. Thus, samples (peptide fractions) were prepared.

Hereafter, measurement was carried out in accordance with a modified version of the method of Kasahara.

Measurement was carried out using the "ACE Color Kit" (Fujirebio, Inc.) in accordance with the attached instructions. Specifically, 50 μl of a sample (a peptide fraction) solution, 50 μl of an enzyme solution (0.1 U/ml ACE, obtained from the rabbit lung, Sigma), and 200 mM borate buffer (pH 8.3) were added to 200 μl of the ACE substrate solution (included in the kit), and the reaction was allowed to proceed at 37° C. for 20 minutes.

Subsequently, 600 μl of a reaction terminator/color developer liquid (included in the kit) was added and mixed therewith, and the resultant was allowed to stand at 37° C. for 3 minutes.

After the color developed, the absorbance at 505 nm was measured.

The ACE inhibitory rate is represented by the following equation.

$$\text{ACE inhibitory rate (\%)} = [1 - (OD_S - OD_{Sb})/(OD_C - OD_{Cb})] \times 100$$

In this case, "$OD_S$" represents the absorbance at 505 nm measured in the manner described above, "$OD_{Sb}$" represents the absorbance observed when 200 mM borate buffer (pH 8.3) was added instead of an enzyme solution, "$OD_C$" represents the absorbance observed when ultrapure water was added instead of a sample solution, and "$OD_{Cb}$" represents the absorbance observed when 200 mM borate buffer (pH 8.3) and ultrapure water were added instead of an enzyme solution and a sample solution, respectively.

In this enzyme reaction system (prior to the addition of the color developer), the concentration (μl/ml) of the sample stock solution exhibiting 50% enzyme activity inhibition was designated as $IC_{50}$, and the value was converted into the concentration of the stock solution before treatment with the Sep-Pak column.

Figure 1:
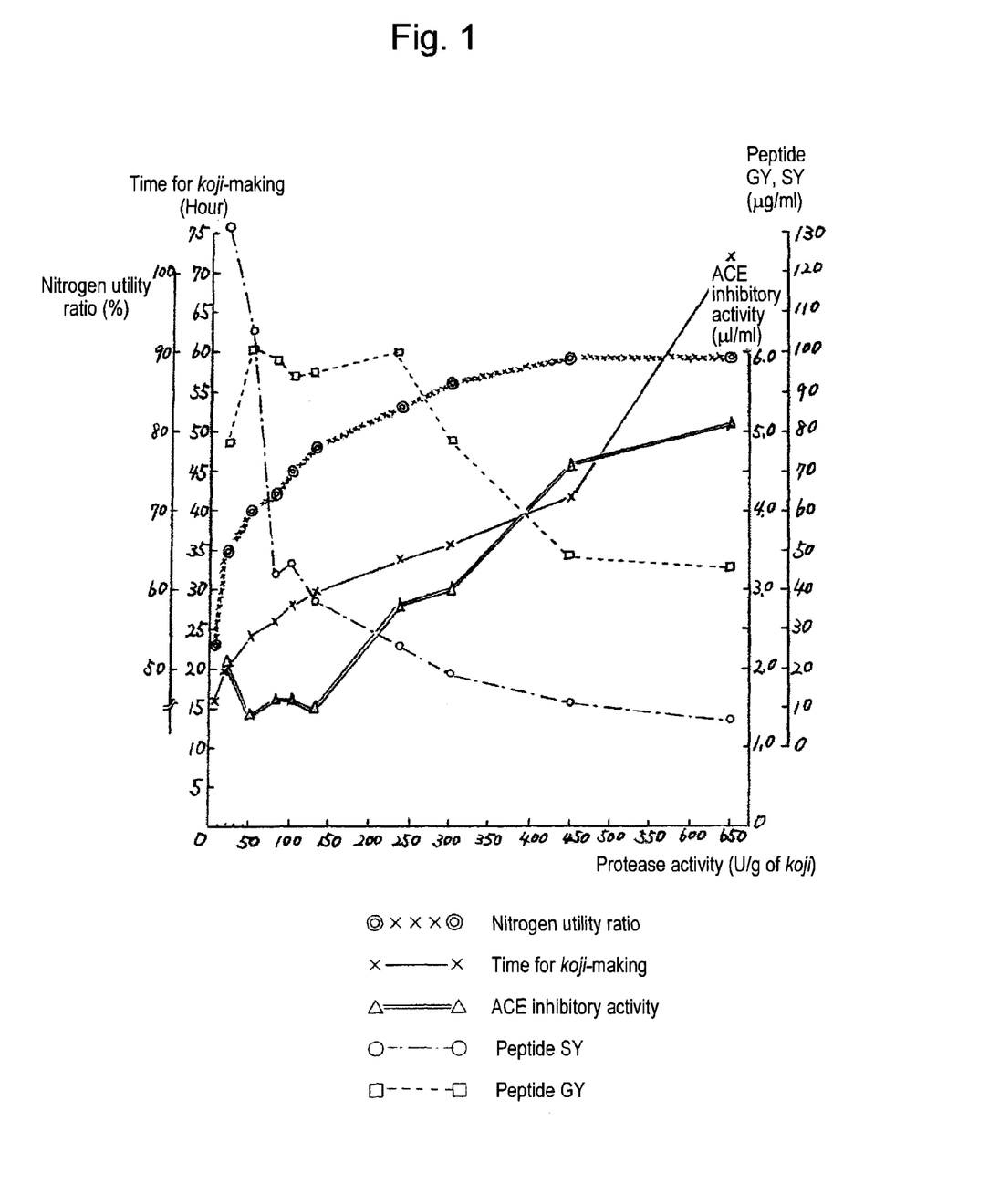
FIG. 1 shows the correlation between protease activity of soy sauce koji and the period of time for koji-making, the nitrogen utility ratio, ACE inhibitory activity, and hypotensive peptide Gly-Tyr (peptide GY) and hypotensive peptide Ser-Tyr (peptide SY).

As is apparent from the results shown in Table 1 and FIG. 1, protease activity of less than 20 U/g koji is not preferable since the nitrogen utility ratio in soy sauce koji would be as low as 53%, that is, the raw material ratio would be lowered. In contrast, protease activity of more than 300 U/g koji would lead to a rapid decrease in hypotensive peptide content and ACE inhibitory activity, and the object of the present invention would not be possible to attain.

Soy sauce koji having protease activity of 20 to 300 U/g koji can produce soy sauce having the following properties: (1) a nitrogen utility ratio of 65% to 86%; (2) hypotensive peptide Gly-Tyr content of 78 μg/ml or more and hypotensive peptide Ser-Tyr content of 20 μg/ml or more; and (3) potent ACE inhibitory activity ($IC_{50}$) of 3.0 μl/ml or less, which is a half or less than that of commercially available low-salt soy sauce (i.e., 6.7 μl/ml).

EXAMPLE 2

Method for Soy Sauce Manufacturing via Heated Digestion

An aqueous common salt solution (about 1.2 liters) was mixed with 0.8 kg of the soy sauce koji having protease activity of 80 U/g koji (Test Group 4) and 235 U/g koji (Test Group 7) prepared in Example 1, so as to bring the common salt concentration in the moromi mash liquid to 13.0% (w/v) after digestion, and the resultant was subjected to digestion at 50° C. for 72 hours while being adequately stirred. Thus, the digested moromi mash was obtained.

The moromi mash was subjected to compression filtration (without lactic acid fermentation or yeast fermentation and maturation), pasteurization, and clarification to obtain heat-digested soy sauce of the Present Inventions 8 and 9.

TABLE 1

| | | Lot Test group | | | | | | | | | | |
|---|---|---|---|---|---|---|---|---|---|---|---|---|
| | | 1 Comparative Example | 2 | 3 | 4 | 5 | 6 | 7 | 8 | 9 Comparative Example | 10 | 11 Control (commercially available |
| | | | | | Present Invention | | | | | | | |
| Item | Name | 1 | 1 | 2 | 3 | 4 | 5 | 6 | 7 | 2 | 3 | soy sauce) |
| Conditions for koji-making | Timing for de-koji (hour) | 16 | 20 | 24 | 26 | 28 | 30 | 34 | 36 | 42 | 72 | — |
| | Protease activity (U/g of koji) | 3 | 20 | 50 | 80 | 100 | 130 | 235 | 300 | 450 | 650 | — |
| Conditions for heated digestion | Temperature (° C.) | 50 | 50 | 50 | 50 | 50 | 50 | 50 | 50 | 50 | 50 | — |
| | Time (hour) | 72 | 72 | 72 | 72 | 72 | 72 | 72 | 72 | 72 | 72 | — |
| Component analysis results | TN % (w/v) | 1.23 | 1.45 | 1.58 | 1.63 | 1.65 | 1.68 | 1.80 | 1.82 | 1.85 | 1.85 | 1.68 |
| | NaCl % (w/v) | 13.2 | 13.0 | 12.9 | 12.7 | 12.5 | 12.5 | 12.1 | 12.2 | 12.1 | 12.1 | 8.2 |
| | Hypotensive peptide GY (μg/ml) | — | 78 | 101 | 98 | 94 | 95 | 100 | 78 | 49 | 46 | 19 |
| | Hypotensive peptide SY (μg/ml) | — | 131 | 105 | 44 | 47 | 37 | 26 | 20 | 12 | 7 | 4 |
| | ACE inhibitory activity ($IC_{50}$) (μl/ml) | — | 2.1 | 1.4 | 1.6 | 1.6 | 1.5 | 2.8 | 3.0 | 4.6 | 5.1 | 6.7 |
| | Nitrogen utility ratio (%) | 53 | 65 | 70 | 72 | 75 | 78 | 83 | 86 | 89 | 89 | — |

For comparison, 0.8 kg of the soy sauce koji having protease activity of 650 U/g koji prepared in Example 1 (Test Group 10) was subjected to heated digestion in the same manner as described above, and heat-digested soy sauce of Comparative Example 4 was obtained in the manner as described above.

The nitrogen utility ratio, the components (TN (total nitrogen) and NaCl), hypotensive peptides, and ACE inhibitory activity of the obtained soy sauce were measured by the method described in Example 1. The results are shown in Table 2.

TABLE 2

| | | Lot | | |
|---|---|---|---|---|
| | | Test group | | |
| | | 4 | 6 | 10 |
| | | Present | Present | Comparative |
| Item | Name | Invention 8 | Invention 9 | Example 4 |
| Conditions for koji-making | Timing for de-koji (hour) | 26 | 34 | 72 |
| | Protease activity | 80 | 235 | 650 |
| Conditions for heated digestion | Temperature (° C.) | 50 | 50 | 50 |
| | Time (hour) | 72 | 72 | 72 |
| Component analysis results | TN % (w/v) | 1.60 | 1.70 | 1.75 |
| | NaCl % (w/v) | 13.0 | 12.9 | 12.6 |
| | GY (µg/ml) | 88 | 104 | 62 |
| | SY (µg/ml) | 43 | 34 | 6 |
| | ACE inhibitory activity ($IC_{50}$) (µl/ml) | 2.5 | 2.8 | 5.00 |
| | Nitrogen utility ratio (%) | 70 | 75 | 85 |

As is apparent from the results of Comparative Example 4 shown in Table 2, when soy sauce koji having high protease activity (i.e., protease activity of 650 U/g koji) is subjected to heated digestion, moromi mash components (proteins, in particular) are rapidly degraded, the raw material utility ratio (in particular, the nitrogen utility ratio) in soy sauce is elevated to about 85% within a short period of time, and the period of time for soy sauce production can be shortened (i.e., fast-brewing). However, soy sauce containing significant amounts of hypotensive peptides Gly-Tyr and Ser-Tyr and having high ACE inhibitory activity cannot be obtained.

When an aqueous common salt solution is mixed with soy sauce koji having low protease activity (i.e., protease activity of 80 U/g koji or 235 U/g koji) and the resultant is subjected to heated digestion, however, soy sauce with a nitrogen utility ratio of about 70% to 75% can be obtained within a short period of time, and soy sauce containing significant amounts of hypotensive peptides Gly-Tyr and Ser-Tyr, which have been known to have hypotensive effects, and having high ACE inhibitory activity can be obtained.

EXPERIMENTAL EXAMPLE 1

Test for Examining Influence of Protease Activity of Soy Sauce Koji and Heated Digestion on Fluctuation of Soy Sauce Peptide Three types of soy sauce products obtained by the method for soy sauce production described below were subjected to measurement of nitrogen utility ratio, components (TN (total nitrogen) and NaCl), hypotensive peptide, and ACE inhibitory activity by the method described in Example 1. The results are shown in Table 3.
(1) Method for Producing Soy Sauce of the Present Invention 5 (See Example 1)
(2) Method for Producing Soy Sauce of Comparative Example 5

Soy sauce was prepared using low-protease soy sauce koji without performing heated digestion.

Specifically, about 1.2 liters of an aqueous common salt solution was mixed with 0.8 kg of soy sauce koji having protease activity of 130 U/g koji (Test Group 6) prepared in Example 1, so as to bring the common salt concentration in the final moromi mash liquid to 15.5% (w/v), lactic acid bacteria (*Tetragenococcus halophilus*) were added at $1 \times 10^5$ cells/g of moromi mash, and lactic acid fermentation was carried out at 20° C. for 1.5 months to obtain soy sauce moromi mash having a pH of about 5.2.

Subsequently, salt-tolerant soy sauce yeast cells (*Zygosaccharomyces rouxii*) were added at $5 \times 10^5$ cells/g of moromi mash, and yeast fermentation and maturation were carried out at 25° C. for 3.5 months while conducting aeration in accordance with a conventional technique, according to need. Subsequently, the moromi mash was subjected to compression filtration, pasteurization, and clarification in accordance with a conventional technique to obtain the soy sauce of Comparative Example 5 with a good flavor.

(3) Method for Producing Soy Sauce of Comparative Example 6

Soy sauce was prepared using high-protease soy sauce koji without performing heated digestion.

Specifically, about 1.2 liters of an aqueous common salt solution was mixed with 0.8 kg of soy sauce koji having protease activity of 650 U/g koji (Test Group 10) prepared in Example 1, so as to bring the common salt concentration in the final moromi mash liquid to 15.5% (w/v), lactic acid bacteria (*Tetragenococcus halophilus*) were added at $1 \times 10^5$ cells/g of moromi mash, and lactic acid fermentation was carried out at 20° C. for 1.5 months to obtain soy sauce moromi mash having a pH of about 5.2.

Subsequently, salt-tolerant soy sauce yeast cells (*Zygosaccharomyces rouxii*) were added at $5 \times 10^5$ cells/g of moromi mash, and yeast fermentation and maturation were carried out at 25° C. for 3.5 months while conducting aeration in accordance with a conventional technique, according to need. Subsequently, the moromi mash was subjected to compression filtration, pasteurization, and clarification in accordance with a conventional technique to obtain the soy sauce of Comparative Example 6 with a good flavor (hereafter, it is referred to as "soy sauce obtained by a conventional technique").

TABLE 3

| Name | | Present Invention 5 | Comparative Example 5 | Comparative Example 6 |
|---|---|---|---|---|
| Conditions for koji-making | Timing for de-koji (hour) | 30 | 30 | 72 |
| | Protease activity | 130 | 130 | 650 |
| Conditions for heated digestion | Temperature (° C.) | 50 | — | — |
| | Time (hour) | 72 | — | — |
| Component analysis results | TN % (w/v) | 1.68 | 1.64 | 1.87 |
| | NaCl % (w/v) | 12.5 | 15.8 | 15.6 |
| | GY (µg/ml) | 95 | 47 | 28 |
| | SY (µg/ml) | 37 | 17 | 4 |
| | ACE inhibitory activity (IC$_{50}$) (µl/ml) | 1.5 | 4.1 | 6.6 |
| | Nitrogen utility ratio (%) | 78 | 78 | 89 |

"GY" represents hypotensive peptide Gly-Tyr and
"SY" represents hypotensive peptide Ser-Tyr.

The following can be understood from the results shown in Table 3. That is, in the case of Present Invention 5 and Comparative Example 5 involving the use of soy sauce koji having low protease activity (i.e., 130 U/g koji), the amounts of hypotensive peptides Gly-Tyr and Ser-Tyr are increased, and ACE inhibitory activity is also enhanced, compared with Comparative Example 6 involving the use of soy sauce koji having high protease activity (i.e., 650 U/g koji). However, in the case of Comparative Example 5 in which heated digestion is not performed, such peptides are degraded into amino acids and gradually disappear as fermentation and maturation of the moromi mash advance. Also, the amounts of hypotensive peptides Gly-Tyr and Ser-Tyr are reduced to a half or less of those in the case of the present invention via degradation.

To the contrary, according to the present invention, soy sauce koji with low protease activity is used and digestion is carried out at high temperatures. Thus, peptides generated and accumulated in the soy sauce moromi mash liquid, and, in particular, hypotensive peptides Gly-Tyr and Ser-Tyr, can be retained in the moromi mash liquid throughout the process from lactic acid fermentation, yeast fermentation, and maturation, to the final moromi mash.

EXPERIMENTAL EXAMPLE 2

Comparison of Peptide Contents in Soy Sauce of the Present Invention 3 and Soy Sauce Obtained by a Conventional Technique Soy sauce of the Present Invention 3 (see Example 1) and soy sauce obtained by a conventional technique (see soy sauce of Comparative Example 6 obtained in Experimental Example 1) were analyzed via high-performance liquid chromatography (hereafter abbreviated as "HPLC," Shimadzu Corporation) to which a Capcell Pak C18 MG III column (4.6×250 mm, Shiseido) was connected.

Gradient elution with acetonitrile concentration of 0% to 30% was carried out at a flow rate of 1 ml/min using an eluate containing 0.1% trifluoroacetic acid (TFA).

The absorbance at 220 nm was detected.

Figure 2:
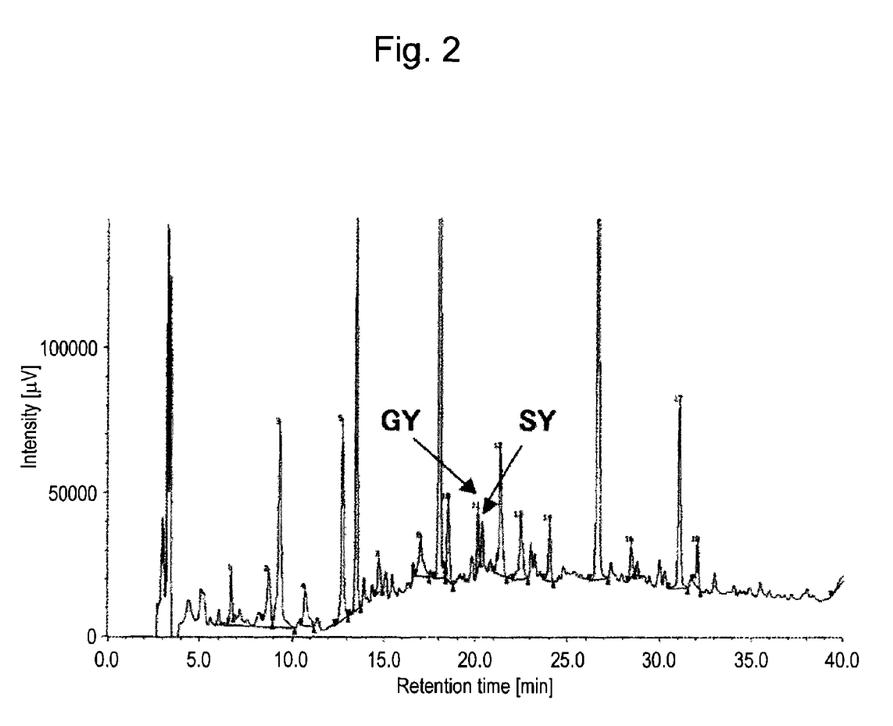
FIG. 2 shows an HPLC chromatogram of the soy sauce according to the present invention.
Figure 3:
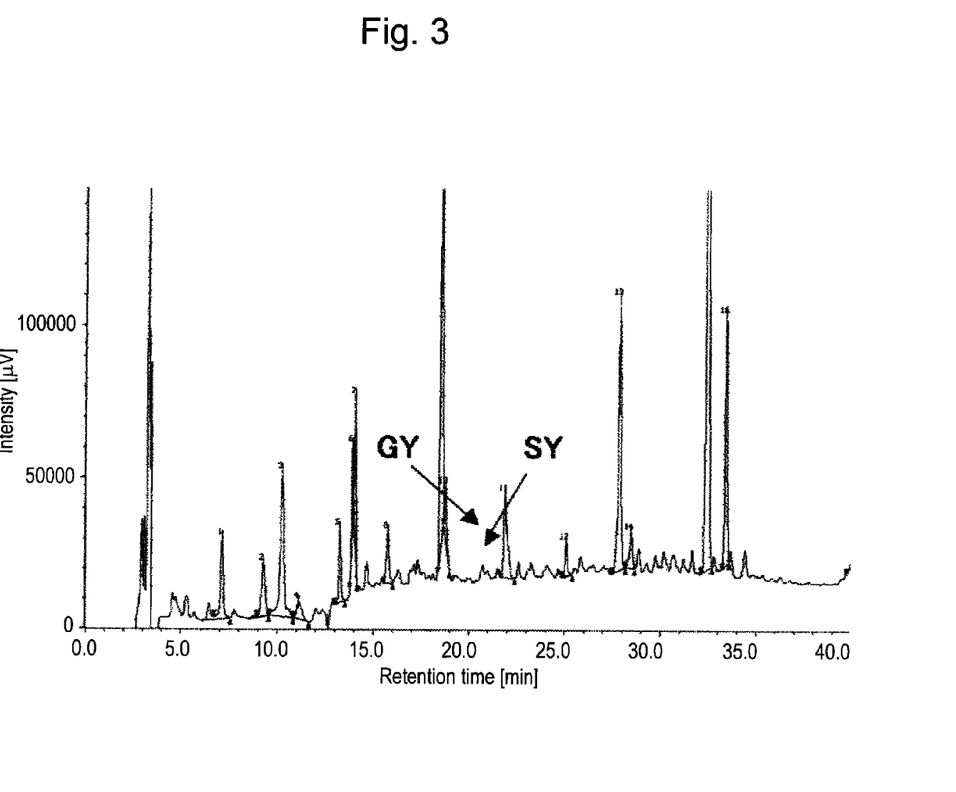
FIG. 3 shows an HPLC chromatogram of soy sauce obtained by a conventional technique.

FIG. 2 and FIG. 3 show the results of measuring peptide content in the soy sauce of the Present Invention 3 and in the soy sauce obtained by a conventional technique. In general, most peaks observed under such analytical conditions are known to be derived from peptides. In FIG. 2 and FIG. 3, however, large peaks observed at 14 minutes, 18 minutes, and 27 minutes were found to be derived from Tyr, Phe, and Trp amino acids, respectively, instead of peptides. It was also confirmed that substantially no other amino acids were retained in the column and such amino acids were eluted within 5 minutes. Accordingly, most peaks observed other than the large peaks observed at 14 minutes, 18 minutes, and 27 minutes are deduced to be derived from peptides.

A comparison of FIG. 2 with FIG. 3 while taking the aforementioned factors into consideration demonstrates that the number and the amount of peptides in the soy sauce of the Present Invention 3 are larger than those of the soy sauce obtained by a conventional technique. In particular, the number and the amount of hypotensive peptides Gly-Tyr and Ser-Tyr in the soy sauce of the Present Invention 3 are significantly larger than those in the soy sauce obtained by a conventional technique.

EXPERIMENTAL EXAMPLE 3

An aqueous common salt solution (about 1.2 liters) was mixed with 0.8 kg of the soy sauce koji having protease activity of 235 U/g koji prepared in Example 1 (Test Group 7) so as to bring the common salt concentration in the moromi mash liquid to 13.0% (w/v) after digestion. Thus, soy sauce moromi mash was prepared.

Subsequently, the resultant was subjected to heated digestion under the temperature and time conditions described in Table 4 to obtain the digested moromi mash.

Hereafter, lactic acid fermentation and yeast fermentation were carried out in the same manner as in Example 1, and the resultants were then subjected to compression filtration and pasteurization, followed by clarification, so as to provide various soy sauce products. The concentration of hypotensive peptides, color, and aroma of the obtained soy sauce products were inspected. The results are shown in FIG. 4

TABLE 4

| | | Hours | | | | |
|---|---|---|---|---|---|---|
| Temperature | | 12 | 24 | 72 | 120 | 168 |
| | | | | Days | | |
| (° C.) | | Half day | 1 day | 3 days | 5 days | 7 days |
| 40 | Hypotensive peptide (*1) | x | x | x | x | x |
| | Color (*2) | ○ | ○ | ○ | ○ | Δ |
| | Aroma (*3) | ○ | ○ | ○ | ○ | Δ |
| 45 | Hypotensive peptide (*1) | x | ○ | ○ | ○ | ○ |
| | Color (*2) | ○ | ○ | ○ | ○ | x |
| | Aroma (*3) | ○ | ○ | ○ | ○ | x |
| 50 | Hypotensive peptide (*1) | x | ○ | ○ | ○ | ○ |
| | Color (*2) | ○ | ○ | ○ | ○ | x |
| | Aroma (*3) | ○ | ○ | ○ | ○ | x |

TABLE 4-continued

| Temper-ature (° C.) | | Hours | | | | |
|---|---|---|---|---|---|---|
| | | 12 | 24 | 72 | 120 | 168 |
| | | | | Days | | |
| | | Half day | 1 day | 3 days | 5 days | 7 days |
| 55 | Hypotensive peptide (*1) | x | ○ | ○ | ○ | ○ |
| | Color (*2) | ○ | ○ | ○ | ○ | x |
| | Aroma (*3) | ○ | ○ | ○ | ○ | x |
| 60 | Hypotensive peptide (*1) | x | ○ | ○ | ○ | ○ |
| | Color (*2) | ○ | Δ | x | x | x |
| | Aroma (*3) | ○ | Δ | x | x | x |

(*1): The symbol "○" indicates the contents of hypotensive peptide Gly-Tyr of 78 μg/ml or more and hypotensive peptide Ser-Tyr of 20 μg/ml or more. The symbol "x" indicates the contents of hypotensive peptide Gly-Tyr of less than 78 μg/ml and/or hypotensive peptide Ser-Tyr of less than 20 μg/ml.
(*2): The symbol "○" indicates No: 10 or greater in terms of the standard color of soy sauce prescribed by JAS, the symbol "Δ" indicates Nos: 5 to 9; and the symbol "x" indicates No: 4 or smaller. A larger color number indicates a lighter color, which is preferred by consumers in recent years.
(*3): The symbol "○" indicates the absence of an odor resulting from warm brewing. The symbol "Δ" indicates the presence of a slight odor resulting from warm brewing. The symbol "x" indicates the presence of an odor resulting from warm brewing.

Based on the results shown in Table 4, peptides generated in the moromi mash gradually disappear as maturation of the moromi mash advances when temperature is lower than 45° C. (e.g., 40° C.) or the time is shorter than 1 day (e.g., half a day), and the peptide content is lowered in the end. Thus, such conditions are not preferable. When temperature is higher than 55° C. (e.g., 60° C.) or the time is longer than 5 days (e.g., 7 days), the color of the digestive liquid is developed and deepened, and the flavor deteriorates due to an odor resulting from warm brewing. Thus, such conditions are not preferable.

EXAMPLE 3

Method for Soy Sauce Production Comprising Performing Heated Digestion, Followed by Lactic Acid Fermentation An aqueous common salt solution (about 1.2 liters) was mixed with 0.8 kg of soy sauce koji having protease activity of 80 U/g koji prepared in Example 1 (Control Group 4), so as to bring the salt concentration in the moromi mash liquid to 13.0% (w/v) after digestion, and the resultant was subjected to digestion at 50° C. for 72 hours while being adequately stirred. Thus, the digested moromi mash was prepared.

Subsequently, the digested moromi mash was cooled to room temperature (about 20° C.), soy sauce lactic acid bacteria (*Tetragenococcus halophilus*) were added at 1×10⁵ cells/g of moromi mash, and lactic acid fermentation was carried out at 20° C. for 3 weeks to obtain soy sauce moromi mash having a pH of about 5.2.

Subsequently, the resultant was subjected to compression filtration, pasteurization, and clarification to obtain soy sauce with adequate acidity and a good flavor.

The analyzed composition of the soy sauce is shown below.

Salt: 13.2% (w/v); total nitrogen: 1.69% (w/v), pH 5.2; hypotensive peptide Gly-Tyr: 92 μg/ml; hypotensive peptide Ser-Tyr: 37 μg/ml; standard color of soy sauce: No. 26.

From the foregoing, it can be understood that soy sauce containing highly concentrated hypotensive peptide and having a good flavor can be obtained by performing high-temperature digestion, followed by lactic acid fermentation according to the present invention.

EXAMPLE 4

Method for Soy Sauce Production Comprising Performing Heated Digestion, Followed by Yeast Fermentation An aqueous common salt solution (about 1.2 liters) was mixed with 0.8 kg of soy sauce koji having protease activity of 80 U/g koji prepared in Example 1 (Control Group 4), so as to bring the salt concentration in the moromi mash liquid to 13.0% (w/v) after digestion, and the resultant was subjected to digestion at 50° C. for 72 hours while being adequately stirred. Thus, the digested moromi mash was prepared.

Subsequently, soy sauce yeast cells (*Zygosaccharomyces rouxii*) were added at 5×10⁵ cells/g of moromi mash, and yeast fermentation and maturation were carried out at 25° C. for 1 month while conducting aeration in accordance with a conventional technique, according to need.

Subsequently, the resultant was subjected to compression filtration, pasteurization, and clarification to obtain soy sauce with an improved aroma and a good flavor.

The analyzed composition of the soy sauce is shown below.

Salt: 13.0% (w/v); total nitrogen: 1.79% (w/v), pH 5.37; hypotensive peptide Gly-Tyr: 94 μg/ml; hypotensive peptide Ser-Tyr: 37 μg/ml; standard color of soy sauce: No. 20

According to the present invention, therefore, soy sauce containing highly concentrated hypotensive peptide and having a good flavor can be obtained by performing high-temperature digestion, followed by yeast fermentation.

EXAMPLE 5

Method for Producing Soy Sauce with High Peptide Content with the Addition of Protein Raw Materials not Subjected to Koji-Making Steamed, defatted soybeans (0.16 kg, 20% (w/w) relative to soy sauce koji) were added to 0.8 kg of soy sauce koji having protease activity of 235 U/g koji prepared in Example 1 (Test group 7), about 1.4 liters of an aqueous common salt solution was mixed therewith, so as to bring the common salt concentration in the moromi mash liquid to 13.0% (w/v) after digestion, and the resultant was subjected to digestion at 50° C. for 72 hours while being adequately stirred. Thus, the digested moromi mash was prepared.

Subsequently, the digested moromi mash was cooled to room temperature (about 20° C.), soy sauce lactic acid bacteria (*Tetragenococcus halophilus*) were added at 1×10⁵ cells/g of moromi mash, and lactic acid fermentation was carried out at 20° C. for 3 weeks to obtain soy sauce moromi mash having a pH of about 5.2.

Subsequently, soy sauce yeast cells (*Zygosaccharomyces rouxii*) were added at 5×10⁵ cells/g of moromi mash, and yeast fermentation and maturation were carried out at 25° C. for 1 month while conducting aeration in accordance with a conventional technique, according to need.

Subsequently, the matured moromi mash was subjected to compression filtration, the resulting raw soy sauce was subjected to pasteurization at 80° C. for 30 minutes, and the resultant was introduced into a clarification tank and subjected to clarification for 3 days therein to obtain soy sauce with good clarity and a flavor.

The analyzed composition of the soy sauce is shown below.

Salt: 13.7% (w/v); total nitrogen: 1.66% (w/v), pH 5.24; hypotensive peptide Gly-Tyr: 101 μg/ml; hypotensive peptide Ser-Tyr: 43 μg/ml; standard color of soy sauce: No. 24

All publications, patents, and patent applications cited herein are incorporated herein by reference in their entirety. In addition, this description includes part or all of the content as disclosed in the description and/or drawings of Japanese Patent Application No. 2009-295466, which is a priority document of the present application.

The invention claimed is:

1. Soy sauce having hypotensive effects obtained by a method comprising mixing (i) soy sauce koji having protease activity of 20 to 300 U/g koji, which does not include additional protein raw material not subjected to koji-making or (ii) soy sauce koji having protease activity of 20 to 300 U/g koji which further comprises not more than 20% (w/w), relative to the soy sauce koji, of a protein raw material not subjected to koji-making, with an aqueous common salt solution to prepare soy sauce moromi mash; and subjecting the soy sauce moromi mash to heated digestion at 45° C. to 55° C. for 1 to 5 days.

2. The soy sauce according to claim 1, comprising angiotensin-I-converting enzyme (ACE)-inhibitory activity ($IC_{50}$) of 3.0 μl/ml or less.

3. The soy sauce according to claim 1 or 2, which comprises 78 μg/ml or more hypotensive peptide Gly-Tyr and 20 μg/ml or more hypotensive peptide Ser-Tyr.

4. A food or beverage product, which comprises the soy sauce according to claim 1.

5. A food or beverage product, which comprises the soy sauce according to claim 2.

6. A food or beverage product, which comprises the soy sauce according to claim 3.

7. A method for manufacturing soy sauce having hypotensive effects comprising:
mixing soy sauce koji having protease activity of 20 to 300 U/g koji with an aqueous common salt solution to prepare soy sauce moromi mash, and subjecting the soy sauce moromi mash to heated digestion at 45° C. to 55° C. for 1 to 5 days.

8. A method for manufacturing soy sauce having hypotensive effects comprising:
mixing soy sauce koji having protease activity of 20 to 300 U/g koji, not more than 20% (w/w) of a protein raw material not subjected to koji-making relative to the soy sauce koji, and an aqueous common salt solution to prepare a soy sauce moromi mash and subjecting the soy sauce moromi mash to heated digestion at 45° C. to 55° C. for 1 to 5 days.

9. The method for manufacturing soy sauce according to claim 7 or 8, which further comprises adding soy sauce lactic acid bacteria and/or yeast cells to the soy sauce moromi mash subjected to heated digestion in the step of heated digestion and subjecting the resultant to fermentation and maturation.

* * * * *